US011511962B2

(12) United States Patent
Neff

(10) Patent No.: US 11,511,962 B2
(45) Date of Patent: Nov. 29, 2022

(54) WINDING HEAD FOR SURGICAL SUTURE MATERIAL

(71) Applicant: Harro Höfliger Verpackungsmaschinen GmbH, Allmersbach im Tal (DE)

(72) Inventor: Ingmar Neff, Allmersbach im Tal (DE)

(73) Assignee: Harro Höfliger Verpackungsmaschinen GmbH, Allmersbach im Tal (DE)

( * ) Notice: Subject to any disclaimer, the term of this patent is extended or adjusted under 35 U.S.C. 154(b) by 408 days.

(21) Appl. No.: 16/850,071

(22) Filed: Apr. 16, 2020

(65) Prior Publication Data

US 2020/0331722 A1 Oct. 22, 2020

(30) Foreign Application Priority Data

Apr. 18, 2019 (EP) ..................................... 19170163

(51) Int. Cl.
*B65H 54/10* (2006.01)
*A61B 17/06* (2006.01)

(52) U.S. Cl.
CPC ....... *B65H 54/10* (2013.01); *A61B 17/06123* (2013.01); *B65H 2701/3918* (2013.01)

(58) Field of Classification Search
CPC ............ B65H 54/10; B65H 2701/3918; A61B 17/06123
See application file for complete search history.

(56) References Cited

U.S. PATENT DOCUMENTS

| 5,012,413 | A | 4/1991 | Sroka et al. |
| 9,908,655 | B2 * | 3/2018 | Martinez ................ B65H 54/44 |
| 2002/0069617 | A1 | 6/2002 | Dey et al. |
| 2016/0317148 | A1 | 11/2016 | Martinez |

* cited by examiner

*Primary Examiner* — William E Dondero
(74) *Attorney, Agent, or Firm* — Smartpat PLC

(57) ABSTRACT

A winding head (10) for surgical suture material has a securing arm (22) and a guide carriage (24), which is mounted on the securing arm (22). In addition, a circumferential guide system (30) is present, which is mounted displaceably on the guide carriage (24). The circumferential guide system (30) has two first tracks (32, 34) which are spaced apart from each other and are connected to each other by two second tracks (36, 38), which are of approximately semi-circular shape. A transition curve is present in at least one of four transition regions (40, 42, 44, 46) between a first track (32, 34) and a second track (36, 38), which transition curve connects the first track (32, 34) and the second track (36, 38) to each other.

10 Claims, 1 Drawing Sheet

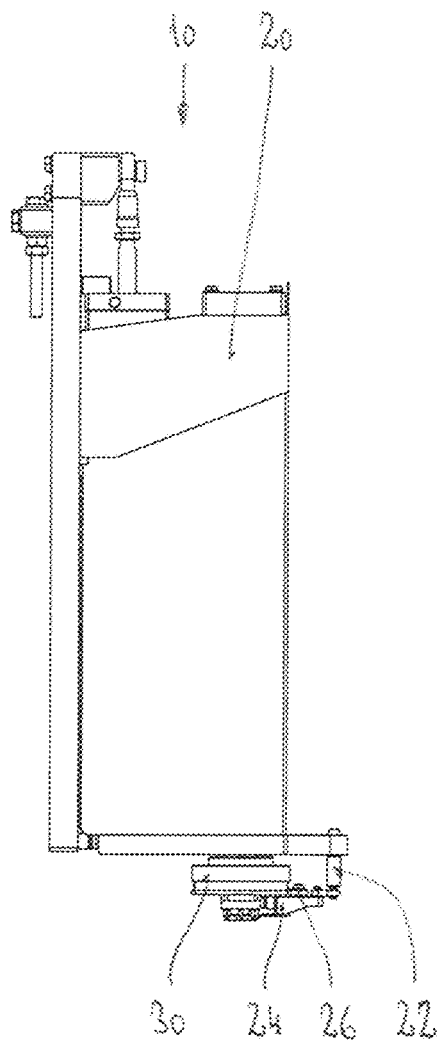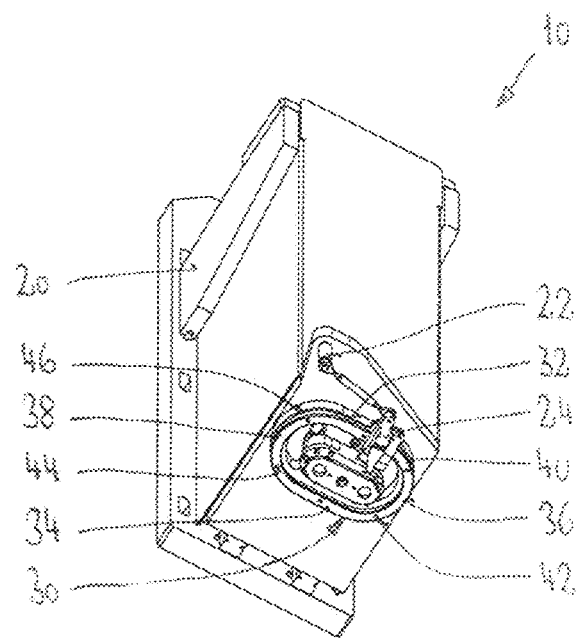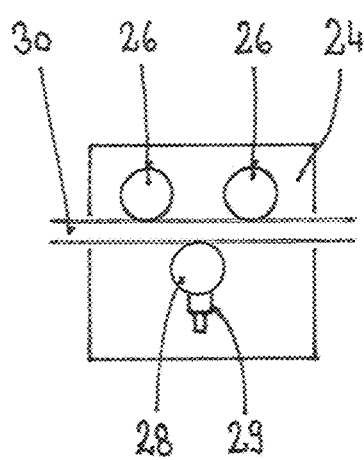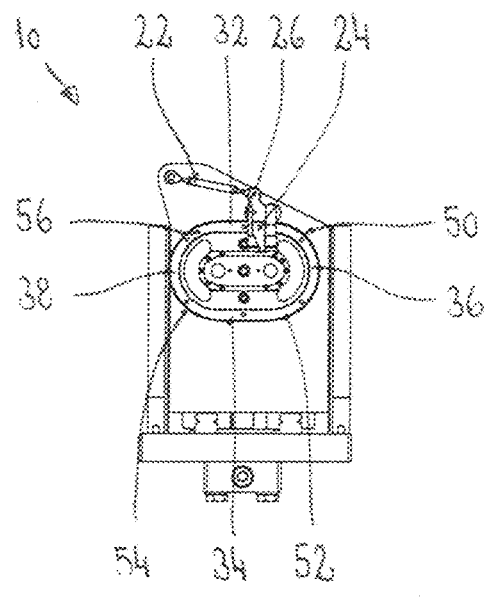

WINDING HEAD FOR SURGICAL SUTURE MATERIAL

TECHNICAL FIELD

The disclosure relates to a winding head for surgical suture material. With such a winding head, a thread of the surgical suture material is wound into a pack. The surgical suture material is removed from this pack for use at a later stage, for example during an operation.

BACKGROUND

Devices for winding surgical suture material into a pack are known. The known devices generally have a winding head via which the actual positioning of the thread of surgical suture material in the pack is effected. The winding heads are generally adapted to the form of the pack and have, at their edge region, a circumferential guide system. A guide carriage with a securing arm is mounted displaceably on the guide system. The securing arm can be statically bound to the winding station provided for it. This winding station can be, for example, a station on a rotary indexing table. The guide carriage travels in a circumferential direction around the guide system, such that the guide system moves in rotation and in so doing winds the surgical suture material into the pack.

Particularly in the case of oval packs, the winding head, and therefore the guide system, also has an oval shape. The guide system thus generally has two semi-circular outer regions, which are preferably connected to each other by two straight stretches running parallel to each other. At the transition between the straight stretches and the semi-circular outer regions, wear increasingly occurs in the form of abrasion and overloading of the guide rollers of the guide carriage. This wear leads to play within the guide, which prevents the exact positioning of the surgical suture material, or at least makes such positioning difficult, such that only low speeds of rotation are possible. The winding head therefore has to be replaced relatively frequently, which leads to a shutdown of the corresponding device and to considerable maintenance costs.

SUMMARY

An object of the disclosure is to make available an improved winding head for surgical suture material, in which wear during operation is kept to a minimum, such that long running times can be achieved with high speeds of rotation.

The object is achieved by the winding head as claimed.

The winding head has a securing arm and a guide carriage, which is mounted on the securing arm. In addition, the winding head has a circumferential guide system, which is mounted displaceably on the guide carriage. During the rotation of the guide system, the surgical suture material is placed in a guided manner into a pack. The guide system has two first tracks which are spaced apart from each other and are connected to each other by two second tracks, which are each approximately semi-circular in shape. Overall, this results in an approximately oval shape of the guide system. A transition curve is present in at least one of the total of four transition regions between a first track and a second track, which transition curve connects the first track and the second track to each other.

By virtue of the fact that the transition from a first, approximately straight track to a second track configured as a curved stretch is modified by such a transition curve, there is no longer an abrupt increase of the transverse acceleration in the region of the transition. Instead, there is now a steady movement, such that load peaks on the roller guides of the guide carriage and on the guide system can be reduced. This leads to smoother running and improved running performance, such that higher winding speeds become possible.

Seen in the running direction of the guide carriage, the greatest loads occur at a transition from an approximately straight first track to an approximately semi-circular second track. Therefore, at least one of these transitions, preferably both transitions, can preferably be equipped with such a transition curve.

If the winding head is intended to permit a winding movement both in the clockwise direction and in the anti-clockwise direction, corresponding transition curves can preferably be provided in all four transition regions.

The at least one transition curve can preferably be configured as a clothoid, as a Bloss curve or as a higher-order curve, such that the movement is modified not abruptly, but instead almost continuously. Clothoids in particular can be exactly calculated mathematically and therefore permit a particularly gentle and wear-free transition.

The two first tracks can in particular be of a straight configuration. In this case, the two first tracks can extend approximately parallel to each other. However, the two first tracks can also extend with a slight curvature and thus have a very large radius. The radius of the two first tracks would in this case be much greater than the radius of the two second tracks. The two first tracks do not necessarily need to have the same radius. The two second tracks can also each have different radii.

In a particularly advantageous embodiment, the guide carriage can have at least one inner guide roller and at least one outer guide roller, between which the guide system is mounted displaceably. At least one of the guide rollers can be mounted resiliently. The resilient mounting of this at least one guide roller ensures that automatic and permanent adjustment of the guide pretensioning between the guide rollers can be achieved. In this way, the maintenance outlay can be reduced. At the same time, the values of the guide pretensioning can be adjusted independently of the experience and instinctive feel of the particular fitter. By virtue of the at least one resiliently mounted guide roller, the winding head can additionally be more tolerant with respect to dimensional deviations of the guide system, which may be caused by manufacturing tolerances. Overall, the wear at the winding head can thus be further reduced.

Further advantages and features of the invention can be gleaned from the features set out in the claims and from the illustrative embodiments below.

BRIEF DESCRIPTION OF THE DRAWINGS

The invention is described and explained in more detail below with reference to the illustrative embodiments in the drawing, in which:

FIG. 1 shows a side view of the winding head, secured to a structural part and having a securing arm and guide carriage.

FIG. 2 shows a perspective view of the winding head according to FIG. 1.

FIG. 3 shows a plan view of the underside of the guide system of the winding head according to FIGS. 1 and 2.

FIG. 4 shows a schematic plan view of the underside of the guide carriage with the guide rollers.

DETAILED DESCRIPTION

The winding head 10 for surgical suture material is shown in FIGS. 1 to 3. A securing arm 22 is mounted movably on a structural part 20. A guide carriage 24 is mounted at the end of the securing arm 22. In the present example, the guide carriage 24 has a plurality of guide rollers 26. With these guide rollers 26, the guide carriage 24 is mounted displaceably on a circumferential guide system 30.

In the present example, the guide carriage 24 (see FIG. 4 in particular) has two outer guide rollers 26 and one inner guide roller 28. The guide system 30 is mounted displaceably between the outer guide rollers 26 and the inner guide roller 28. In the present example, the inner guide roller 28 is secured to the guide carriage via a spring arrangement 29, such that said guide roller 28 is mounted resiliently. In this way, automatic and permanent adjustment of the guide pretensioning between the guide rollers 26, 28 can be achieved. This can reduce considerably the maintenance outlay for the guide rollers 26, 28 and therefore also for the guide carriage 24. In addition, the winding head is in this way more tolerant with respect to dimensional deviations of the guide system, which may be caused by manufacturing tolerances.

The circumferential guide system 30 (see FIG. 3 in particular) has two first tracks 32, 34 which, in the present example, are of a straight configuration and run parallel to each other. The two first tracks 32, 34 are connected to each other by two approximately semi-circular second tracks 36, 38. Overall, this results in an approximately oval shape of the guide system 30.

The guide system 30 is generally adapted in form to the outer contour of the pack into which the surgical suture material to be wound is intended to be placed. Depending on the outer contour of this pack, the two first tracks 32, 34 may also not run parallel to each other and/or may not be straight, and instead they can run in an arc with a large radius of curvature. Moreover, the two second tracks 36, 38 do not each need to have identical radii.

The form of the guide system 30, with two first tracks 32, 34 and two second tracks 36, 38, results overall in four transition regions 40, 42, 44, 46. If the first tracks 32, 34 and the second tracks 36, 38 were to adjoin each other in these transition regions 40, 42, 44, 46 without further measures, there would be an abrupt change of the movement (from straight to curved or from curved to straight). This would lead to increased wear of the guide rollers 26, 28 of the guide carriage 24, such that the guide carriage 24 would have to be regularly serviced and exchanged. In addition, the guide system 30 itself would also be exposed to increased abrasion in these transition regions 40, 42, 44, 46, such that regular replacement would also have to be carried out here.

Therefore, in the present example, all four transition regions 40, 42, 44, 46 are provided with a respective transition curve 50, 52, 54, 56. The transition curves 50, 52, 54, 56 do not have a constant radius, and instead the curvature of the transition curves 50, 52, 54, 56 changes over their entire profile, such that a gentle transition of the first tracks 32, 34 to the second tracks 36, 38, and vice versa, is possible. This permits an almost continuous change of the movement, which is particularly gentle on the guide rollers 26, 28 of the guide carriage 24 and also on the guide system 30.

The wear on the guide rollers 26, 28 is greatest at the transition regions 40, 44, where a straight track 32, 34 transitions into a curved track 36, 38. Therefore, a transition curve 50, 54 should be provided in particular at these transition regions 40, 44. If rotation is intended to be possible in the clockwise direction and in the anti-clockwise direction, a corresponding transition curve 50, 52, 54, 56 should be provided at all four transition regions 40, 42, 44, 46.

The invention claimed is:

1. A winding head (10) for surgical suture material, comprising:
   a securing arm (22);
   a guide carriage (24), which is mounted on the securing arm (22); and
   a circumferential guide system (30), which is mounted displaceably on the guide carriage (24);
   wherein the circumferential guide system (30) has two first tracks (32, 34) which are spaced apart from each other,
   wherein the two first tracks (32, 34) of the circumferential guide system (30) are connected to each other by two second tracks (36, 38), which are of approximately semi-circular shape, and
   wherein a transition curve (50, 52, 54, 56) having a non-constant radius is present in at least one of four transition regions (40, 42, 44, 46) between the two first tracks (32, 34) and the two second tracks (36, 38), which transition curve (50, 52, 54, 56) connects one of the two first tracks (32, 34) and one of the two second tracks (36, 38) to each other.

2. The winding head according to claim 1, wherein the transition curve (50, 54) is arranged in one of the transition regions (40, 44) from a first track (32, 34) to a second track (46, 48) along a direction of travel of the guide carriage (24).

3. The winding head according to claim 2, wherein in all four transition regions (40, 42, 44, 46) between the two first tracks (32, 34) and the two second tracks (36, 38) a respective transition curve (50, 52, 54, 56) is present which connects a respective one of the two first tracks (32, 34) and a respective one of the two second tracks (36, 38) to each other.

4. The winding head according to claim 1, wherein the transition curve (50, 52, 54, 56) is configured as a clothoid.

5. The winding head according to claim 1, wherein the two first tracks (32, 34) run approximately parallel to each other.

6. The winding head according to claim 1, wherein the guide carriage (24) has at least one inner guide roller (28) and at least one outer guide roller (26), between which the circumferential guide system (30) is displaceably mounted, and
   wherein at least one of the guide rollers (26, 28) is mounted resiliently.

7. The winding head according to claim 6, wherein the at least one inner guide roller (28) is mounted resiliently.

8. The winding head according to claim 1, wherein the transition curve (50, 52, 54, 56) is configured as a Bloss curve.

9. The winding head according to claim 1, wherein the transition curve (50, 52, 54, 56) is configured as a higher-order curve.

10. The winding head according to claim 1, wherein the guide carriage (24) has one inner guide roller (28) and two outer guide rollers (26), between which the circumferential guide system (30) is displaceably mounted.

* * * * *